United States Patent [19]

Imaki et al.

[11] Patent Number: 4,667,047
[45] Date of Patent: May 19, 1987

[54] METHOD FOR PRODUCING MONOSILANE AND A TETRAALKOXYSILANE

[75] Inventors: Naoshi Imaki, Atsugi; Junzo Haji, Yokohama; Yoko Misu, Tokyo, all of Japan

[73] Assignee: Mitsubishi Chemical Industries Limited, Tokyo, Japan

[21] Appl. No.: 860,572

[22] Filed: May 7, 1986

[30] Foreign Application Priority Data

May 16, 1985 [JP] Japan ................. 60-104778
May 22, 1985 [JP] Japan ................. 60-109890
Jun. 4, 1985 [JP] Japan ................. 60-120775

[51] Int. Cl.⁴ ............................. C07F 7/08; C07F 7/18
[52] U.S. Cl. ....................................................... 556/469
[58] Field of Search ........................................ 556/469

[56] References Cited

U.S. PATENT DOCUMENTS

| | | | |
|---|---|---|---|
| 3,374,247 | 3/1968 | Pepe et al. ............... | 556/469 X |
| 3,384,652 | 5/1968 | Hamilton ................. | 556/469 |
| 3,829,555 | 8/1974 | Muraoka et al. .......... | 556/469 X |
| 4,016,188 | 4/1977 | Kotzsch et al. .......... | 556/469 X |

FOREIGN PATENT DOCUMENTS

| | | | |
|---|---|---|---|
| 0146148 | 6/1985 | European Pat. Off. ............ | 556/469 |
| 0147834 | 7/1985 | European Pat. Off. ............ | 556/469 |
| 49-27517 | 7/1974 | Japan .................. | 556/469 |
| 49-130397 | 12/1974 | Japan .................. | 556/469 |
| 50-7800 | 1/1975 | Japan .................. | 556/469 |
| 0707225 | 2/1983 | U.S.S.R. ............... | 556/469 |

*Primary Examiner*—Paul F. Shaver
*Attorney, Agent, or Firm*—Oblon, Fisher, Spivak, McClelland & Maier

[57] ABSTRACT

A method for producing monosilane and a tetraalkoxysilane by disproportionation of an alkoxysilane, which comprises contacting an alkoxysilane having the formula:

$$H_nSi(OR)_{4-n} \qquad (I)$$

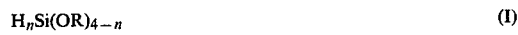

wherein R is a lower alkyl group and n is an integer of 1 to 3, with a catalyst selected from the group consisting of a platinum group metal, a compound of a platinum group metal, an anion exchange resin, alumina, silica alumina and zeolite containing a metal of Group Ia of the periodic table.

11 Claims, No Drawings

METHOD FOR PRODUCING MONOSILANE AND A TETRAALKOXYSILANE

The present invention relates to a method for producing monosilane and a tetra lower alkoxysilane by disproportionation of an alkoxysilane.

Monosilane is useful as a highly pure silicon material for the production of semiconductors, and it also finds a wide range of applications as a starting material for example amorphous silicon photosensitive materials, solar cells or ceramic materials.

Various methods are known for the production of monosilane including a method wherein magnesium silicide is reacted with dilute hydrochloric acid or ammonium bromide, a method wherein silicon chloride is reduced by LiAlH$_4$, and a method for disproportionation of an alkoxysilane. According to the method for disproportionation of an alkoxysilane, it is usual to employ a triethoxysilane as the starting material, whereby monosilane and a tetraethoxysilane are produced simultaneously as shown by the following formula:

$$4SiH(OC_2H_5)_3 \rightarrow SiH_4 + 3Si(OC_2H_5)_4$$

Sodium used to be employed as the catalyst for the disproportionation reaction. However, the yield was so low that the method was not practically useful.

Japanese Examined Patent Publication No. 20040/1976 proposes a method for producing monosilane by disproportionation of triethoxysilane by using sodium ethoxide as the catalyst. This method has a merit in that the catalytic efficiency is high. However, the catalyst is soluble in ethoxysilane, and accordingly, there is a problem in the separation of tetraethoxysilane and the catalyst after the reaction.

The tetraalkoxysilane formed at the same time as monosilane, is also useful as a pure silicon material for the production of various silicon compounds useful for example optical fibers, photomasks or sealing agents for IC. Therefore, it is desired to obtain the alkoxysilane in high purity by readily separating it from the catalyst.

The present inventors have conducted extensive researches with an aim to develop a catalyst which has a high reaction efficiency in the method for the production of silane and a tetraalkoxysilane by disproportionation of an alkoxysilane and which can readily be separated from the reaction products, and as a result, have found that a certain solid catalyst satisfies the requirements. The present invention is based on this discovery.

The present invention provides a method for producing monosilane and a tetraalkoxysilane by disproportionation of an alkoxysilane, which comprises contacting an alkoxysilane having the formula:

$$H_nSi(OR)_{4-n} \qquad (I)$$

wherein R is a lower alkyl group and n is an integer of 1 to 3, with a catalyst selected from the group consisting of a platinum group metal, a compound of a platinum group metal, an anion exchange resin, alumina, silica alumina and zeolite containing a metal of Group Ia of the periodic table.

Now, the present invention will be described in detail with reference to the preferred embodiments.

The present invention is concerned with a disproportionation reaction represented by the following formula:

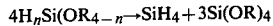

$$4H_nSi(OR)_{4-n} \rightarrow SiH_4 + 3Si(OR)_4$$

wherein R is a lower alkyl group and n is an integer of 1 to 3.

The starting material $H_nSi(OR)_{4-n}$ for the present invention includes a monoalkoxysilane, a dialkoxysilane and a trialkoxysilane wherein R is a lower alkyl group such as an alkyl group having from 1 to 6 carbon atoms, preferably from 1 to 3 carbon atoms. These silanes may be used alone or in combination as a mixture. Specifically, there may be mentioned monomethoxysilane, dimethoxysilane, trimethoxysilane, monoethoxysilane, diethoxysilane, triethoxysilane, tri-i-propoxysilane and tri-sec-butoxysilane. Among them, trimethoxysilane, triethoxysilane and tri-i-propoxysilane are preferred.

The catalyst for the method of the present invention is selected from the group consisting of a platinum group metal, a compound thereof, an anion exchange resin, alumina, silica alumina and zeolite containing a metal of Group Ia of the periodic table. Specifically, there may be employed ruthenium, rhodium, palladium, osmium, iridium and platinum metals, or their compounds. When used in the form of a metal, it may be supported on a carrier. It is particularly preferred that noble metals such as Ru, Rh, Pd and Pt are supported on a carrier such as active carbon, alumina, silica or barium carbonate. As the compounds of these metals, various compounds may be employed so long as they are substantially insoluble in the starting material alkoxysilane and in the reaction products. For instance, there may be mentioned inorganic acid salts such as nitrates or sulfates, organic acid salts such as acetates, and oxides of such metals. Their halides likewise show catalytic activities, but may be undesirable depending upon the purpose of the products, since the products are likely to be contaminated with halogen ions.

The anion exchange resin to be used as a catalyst of the present invention is a resin containing primary to tertiary amine groups (weakly basic type) or quaternary ammonium groups (strongly basic type) as ion exchange groups bonded to a three-dimensionally polymerized polymer substrate. In the present invention, anion exchange resins of both weakly basic type and strongly basic type may be employed. As a typical representative of the polymer substrate, a copolymer of styrene and divinylbenzene may be mentioned.

Ion exchange resins are classified depending upon the degree of crosslinking into low crosslinking resins having a degree of crosslinking of at most 8% and high crosslinking resins having a degree of crosslinking higher than 8%. In the present invention, both types may be employed. Further, they may be classified structurally depending upon the porosity into gel-type, porous type and highly porous type resins, and any one of such types may be used in the present invention. Commercially available anion exchange resins are usually in the form of chemically stable chloride salt (R-N.Cl), and it is common to regenerate them in the form of hydroxide (R-N.OH) by using a NaOH solution at the time of their use. In the method of the present invention, they may be used in either chloride-form or hydroxide-form.

As specific examples of commercially available anion exchange resins, there may be mentioned DIAION ® SA-10A, HPA-25, PA-306, WA-20 and WA-30 manufactured and sold by Mitsubishi Chemical Industries Co., Ltd.

As specific examples of the alumina, there may be mentioned α-alumina, γ-alumina, η-alumina, θ-alumina, δ-alumina, χ-alumina, active alumina, boehmite and boehmite gel.

As the silica alumina, preferred is a silica alumina containing from 10 to 90% of silica.

The zeolite containing a metal of Group Ia of the periodic table may be of NaY, KA, KY, CsY, RbY, NaX, Na mordenite, KL and NaZSM-5 types.

Among the above catalysts, particularly preferred are alumina and zeolite, particularly zeolite of KA type.

These catalysts are effective for the purpose of the present invention when used in an amount of at least 0.01% by weight relative to the alkoxysilane as the starting material. However, it is usual to employ them in an amount of from 0.01 to 200% by weight, preferably from 0.1 to 50% by weight.

The reaction may be conducted in a batch system or in a continuous system. According to the method of the present invention, the starting material contains no halogen, and the method can be conducted without any particular restrictions as to the material for the apparatus. Therefore, the type of the reaction system can freely be selected to be suitable for the type of the catalyst.

The reaction can be conducted at room temperature under atmospheric pressure. However, it is usually preferred to conduct the reaction under heating under atmospheric pressure. The method of the present invention is not very much affected by the temperature. However, the preferred temperature is within a range of from 50° to 80° C.

With respect to the reaction pressure, the method can be conducted under an optional pressure from a reduced pressure to an elevated pressure. However, the monosilane product is likely to be ignited instantly when brought in contact with air, and it is preferred to conduct the operation under atmospheric pressure.

No solvent is required for the reaction. However, tetraalkoxysilane as one of the reaction products of the disproportionation, or other substances including aliphatic saturated hydrocarbons such as hexane and heptane, and alicyclic saturated hydrocarbons such as cyclohexane, may be employed as the solvent.

The reaction is conducted usually in an inert gas atmosphere such as nitrogen or argon. The use of nitrogen is particularly preferred when the resulting monosilane is to be condensed and collected.

Monosilane formed by the reaction has a boiling point of $-111.9°$ C., and is withdrawn from the reactor and collected in the form of a gas. On the other hand, the tetraalkoxysilane remains in the reactor.

The above-mentioned catalyst to be used in the present invention is substantially insoluble in the starting material and in the reaction products. After the reaction, the catalyst can readily be separated from the tetraalkoxysilane as the reaction product.

Now, the present invention will be described in further detail with reference to the Examples. However, it should be understood that the present invention is by no means restricted to such specific Examples.

EXAMPLE 1

Into a pressure glass autoclave having an internal capacity of 100 ml equipped with a stirrer, a nitrogen gas supply tube, a gas discharge tube provided with a condenser and a liquid feed tube, 6.3 g of an α-alumina catalyst (KMS manufactured by Sumitomo Chemical) preliminarily pulverized and dried in a nitrogen stream under heating, was charged, and the interior of the autoclave was thoroughly purged with nitrogen Then, 0.2 mol of trimethoxysilane was introduced from a liquid feed tube at room temperature, and the stirring was initiated.

The reaction started at room temperature when the catalyst and trimethoxysilane were brought in contact with each other to form monosilane. Then, the temperature was raised to 70° C., and the reaction was continued for six hours until monosilane no longer formed. The formed monosilane was withdrawn from the gas discharge tube, and quantitatively analyzed by gas chromatography as time passed. As a result, the conversion of trimethoxysilane was 79 mol %, the amount of monosilane formed was 0.0395 mol and the amount of tetramethoxysilane formed was 0.118 mol.

After the reaction, the reaction product was filtered to separate the catalyst. The catalyst was insoluble in the starting material and in the reaction products, and was readily separated.

EXAMPLES 2 to 6

The reaction was conducted in the same manner as in Example 1 except that the type and amount of the catalyst and the reaction time were changed. The results of the reaction are shown in Table 1.

Each catalyst was insoluble in the starting material and the reaction products, and was easily separated by filtration of the reaction products.

TABLE 1

| Example No. | Catalyst (manufacturers) | Amount of the catalyst (g) | Reaction time (hr) | TMSH *1 conversion (mol %) | Amount of $SiH_4$ formed (mol) | Amount of *2 QMS formed (mol) |
| --- | --- | --- | --- | --- | --- | --- |
| 2 | γ-Alumina (SCM-250 manufactured by Rhone Poulenc) | 6.5 | 2.4 | 90.9 | 0.0455 | 0.136 |
| 3 | Active alumina (KHA-46 manufactured by Nishio Kogyo) | 6.5 | 3.3 | 90.7 | 0.0454 | 0.136 |
| 4 | Silica-alumina (N633-Hu manufactured by Nikki) | 2.8 | 5.0 | 84.1 | 0.0420 | 0.126 |
| 5 | Molecular Sieve-3A *3 (manufactured by Union Showa) | 5.7 | 2.4 | 88.3 | 0.0441 | 0.132 |
| 6 | Molecular Sieve-13X *4 | 5.7 | 6.3 | 75.0 | 0.0375 | 0.112 |

TABLE 1-continued

| Example No. | Catalyst (manufacturers) | Amount of the catalyst (g) | Reaction time (hr) | TMSH *1 conversion (mol %) | Amount of SiH4 formed (mol) | Amount of *2 QMS formed (mol) |
|---|---|---|---|---|---|---|
| | (manufactured by Union Showa) | | | | | |

*1: TMSH: Trimethoxysilane
*2: QMS: Tetramethoxysilane

TMSH conversion = $\left(1 - \dfrac{\text{Unreacted TMSH mol}}{\text{Charged TMSH mol}}\right) \times 100$

*3: KA-type zeolite
*4: NaX-type zeolite

EXAMPLE 7

Into the same pressure glass autoclave as used in Example 1, 3.5 g of an anion exchange resin (DIAION®-WA-30, manufactured by Mitsubishi Chemical Industries Co., Ltd) dried in a nitrogen stream under heating, was charged, and the interior of the autoclave was thoroughly purged with nitrogen. Then, 0.2 mol of trimethoxysilane was added through a liquid feed tube at room temperature, and the stirring was initiated.

The reaction started at room temperature when the catalyst and trimethoxysilane were brought in contact with each other to form monosilane. Then, the temperature was raised to 55° C., and the reaction was continued for 1 hour until monosilane no longer formed. The formed monosilane was quantitatively analyzed by gas chromatography as time passed. As a result, the conversion of trimethoxysilane was 97.5 mol %, the amount of the formed monosilane was 0.0487 mol and the amount of the formed tetramethoxysilane was 0.146 mol.

After the reaction, the reaction products were filtered, and the catalyst was separated. The catalyst was insoluble in the starting material and in the reaction products, and was easily separated from the reaction products.

EXAMPLES 8 and 9

The reaction was conducted in the same manner as in Example 7 except that the type (each manufactured by Mitsubishi Chemical Industries Co., Ltd.) and amount of the anion exchange resin and the reaction time were changed. The results are shown in Table 2. The physical properties of the anion exchange resin used as the catalyst are shown in Table 3.

Each anion exchange resin was insoluble in the starting material and in the reaction products, and was easily separated by the filtration of the reaction products.

TABLE 2

| Example No. | Catalyst (manufacturers) | Amount of the catalyst (g) | Reaction time (hr) | TMSH *1 conversion (mol %) | Amount of SiH4 formed (mol) | Amount of *2 QMS formed (mol) |
|---|---|---|---|---|---|---|
| 8 | DIAION PA-306 | 5.2 | 0.7 | 60.4 | 0.0302 | 0.0906 |
| 9 | DIAION HPA-25 | 0.7 | 1.0 | 60.4 | 0.0302 | 0.0906 |

TABLE 3

| | Brand name | | |
|---|---|---|---|
| | DIAION WA-30 | DIAION PA-306 | DIAION HPA-25 |
| Features | Styrene-type weakly basic anion exchange resin | Styrene-type strongly basic anion exchange resin | Styrene-type strongly basic anion exchange resin |
| | Porous type | Porous type | Highly porous type |
| Form of counter ions | OH form | OH form | Cl form |
| Apparent density (g/l) | 615 | 645 | 682 |
| Ion exchange capacity (meq/ml) | 1.5 or more | 0.8 or more | 0.7 or more |
| Effective diameter (mm) | 0.35–0.55 | 0.35–0.55 | 0.4 |
| Durable temperature (°C.) | Not higher than 100° C. | Not higher than 60° C. | Not higher than 60° C. |
| Functional groups | Tertiary amine | Quaternary ammonium | Quaternary ammonium |

EXAMPLES 10 to 12

In the same manner as in Example 1, the disproportion reaction of trimethoxysilane was conducted by using the catalyst and reaction conditions as identified in Table 4. The results are shown in Table 4.

TABLE 4

| Example No. | Catalyst (manufacturers) | Amount of the catalyst (g) | Reaction time (hr) | TMSH *1 conversion (mol %) | Amount of SiH4 formed (mol) | Amount of *2 QMS formed (mol) |
|---|---|---|---|---|---|---|
| 10 | 2% Ru-supported on Al2O3 (manufactured by Nippon Engelhard) | 1.9 | 4.3 | 64.4 | 0.0322 | 0.096 |
| 11 | 2% Pd-supported on active carbon (manufactured by Nippon Engelhard) | 5.0 | 4.8 | 64.1 | 0.0320 | 0.096 |
| 12 | 5% Pd-supported on BaCO3 (manufactured by Nippon Engelhard) | 4.8 | 4.0 | 80.3 | 0.0402 | 0.12 |

EXAMPLE 13

Into a Pyrex glass reactor having an inner diameter of 12 mm and a length of 200 mm and equipped with a nitrogen supply tube, a liquid feed tube and a thermometer, 10 g of a preliminarily thoroughly dried 2% Ru-supported alumina catalyst manufactured by Nippon Engelhard, was packed and heated to 70° C. under a nitrogen stream.

Then, trimethoxysilane was continuously charged at a rate of 0.2 mol/hr.

The reaction was continued for 6 hours. During the period, the liquid component collected from the reactor by an overflow system and the gas component formed, were quantitatively analyzed by gas chromatography independently. As the catalytic performance upon expiration of 3 hours and 6 hours, the trimethoxysilane conversion was 43 mol % and 33 mol %, respectively, and the amount of monosilane formed was 0.0215 mol and 0.0165 mol, respectively. Further, the amount of tetramethoxysilane formed, was 0.0645 mol and 0.0495 mol, respectively.

EXAMPLES 14 to 16

The reaction was conducted in the same manner as in Example 13 except that the type and amount of the catalyst and the reaction time were changed. The results are shown in Table 5.

TABLE 5

| Example No. | Catalyst (manufacturers) | Amount of the catalyst (g) | Reaction time (hr) | TMSH *1 conversion (mol %) | Amount of SiH$_4$ formed (mol) | Amount of *2 QMS formed (mol) |
|---|---|---|---|---|---|---|
| 14 | 0.5% Rh-supported on Al$_2$O$_3$ (manufactured by Nippon Engelhard) | 9.7 | 1<br>3 | 45<br>42 | 0.023<br>0.021 | 0.069<br>0.063 |
| 15 | 0.5% Pd-supported on Al$_2$O$_3$ carbon (manufactured by Nippon Engelhard) | 9.1 | 2<br>4 | 38<br>44 | 0.019<br>0.022 | 0.057<br>0.066 |
| 16 | 2% Pt-supported on Al$_2$O$_3$ (manufactured by Nippon Engelhard) | 10.2 | 3<br>5 | 27<br>22 | 0.0135<br>0.011 | 0.0405<br>0.033 |

As described in the foregoing, according to the method of the present invention, monosilane and a tetraalkoxysilane can readily be obtained in good yield from an alkoxysilane. The catalyst used in the present invention is substantially insoluble in the reaction products, and accordingly the separation of the catalyst from the reaction product is quite easy. In the method of the present invention, an alkoxysilane containing no halogen is used as the starting material, and therefore there is no particular restriction as to the material of which the reaction apparatus is made, whereby it is possible to obtain monosilane having no contamination due to halogens. Further, it is possible to obtain a tetraalkoxysilane free from being contaminated by the catalyst.

We claim:

1. A method for producing monosilane and a tetraalkoxysilane by disproportionation of an alkoxysilane, which comprises contacting an alkoxysilane having the formula:

$$H_nSi(OR)_{4-n} \qquad (I)$$

wherein R is a lower alkyl group and n is an integer of 1 to 3, with a catalyst selected from the group consisting of a platinum group metal, a compound of a platinum group metal, an anion exchange resin, alumina, silica alumina and zeolite containing a metal of Group Ia of the periodic table.

2. The method according to claim 1, wherein the catalyst is used in an amount of from 0.01 to 200% by weight relative to the alkoxysilane as the starting material.

3. The method according to claim 2, wherein the catalyst is used in an amount of from 0.1 to 50% by weight relative to the alkoxysilane.

4. The method according to claim 2, wherein the catalyst is alumina.

5. The method according to claim 1, wherein the catalyst is zeolite containing a metal of Group Ia of the periodic table.

6. The method according to claim 5, wherein the zeolite is of KA type.

7. The method according to claim 1, wherein the catalyst is a platinum metal or its compound.

8. The method according to claim 1, wherein the catalyst is an anion exchange resin.

9. The method according to claim 1, wherein R in the alkoxysilane of the formula I is an alkyl group having from 1 to 6 carbon atoms.

10. The method according to claim 1, wherein the alkoxysilane of formula I is a trialkoxysilane with n being 1.

11. The method according to claim 1, wherein the alkoxysilane of formula I is trimethoxysilane.

* * * * *